US012569612B2

(12) United States Patent
Rowe

(10) Patent No.: US 12,569,612 B2
(45) Date of Patent: Mar. 10, 2026

(54) METHOD FOR DISINFECTING AN ANAL IRRIGATION SYSTEM

(71) Applicant: Coloplast A/S, Humlebaek (DK)

(72) Inventor: Ian James Rowe, Vaerloese (DK)

(73) Assignee: Coloplast A/S, Humlebaek (DK)

( * ) Notice: Subject to any disclaimer, the term of this patent is extended or adjusted under 35 U.S.C. 154(b) by 463 days.

(21) Appl. No.: 17/600,129

(22) PCT Filed: Apr. 3, 2020

(86) PCT No.: PCT/DK2020/050091
§ 371 (c)(1),
(2) Date: Sep. 30, 2021

(87) PCT Pub. No.: WO2020/200390
PCT Pub. Date: Oct. 8, 2020

(65) Prior Publication Data
US 2022/0160953 A1 May 26, 2022

(30) Foreign Application Priority Data
Apr. 5, 2019 (DK) ............................ PA 2019 70217

(51) Int. Cl.
*A61M 3/02* (2006.01)
*A61L 2/18* (2006.01)
*B08B 9/032* (2006.01)

(52) U.S. Cl.
CPC ................. *A61M 3/02* (2013.01); *A61L 2/18* (2013.01); *A61M 3/0202* (2021.05); *A61M 3/0229* (2013.01); *A61M 3/0258* (2013.01);

*A61M 3/0279* (2013.01); *B08B 9/0321* (2013.01); *A61L 2202/17* (2013.01);
(Continued)

(58) Field of Classification Search
CPC ........................ A61M 3/0229; A61M 2209/10
See application file for complete search history.

(56) References Cited

U.S. PATENT DOCUMENTS

| | | | |
|---|---|---|---|
| 2,832,341 A | | 4/1958 | Stack |
| 4,637,814 A | * | 1/1987 | Leiboff ............... A61M 3/0283 |
| | | | 604/27 |
| 4,682,979 A | | 7/1987 | Girouard |

(Continued)

FOREIGN PATENT DOCUMENTS

| | | |
|---|---|---|
| FR | 1494832 A | 9/1967 |
| WO | 9004983 A1 | 5/1990 |

(Continued)

*Primary Examiner* — Natasha N Campbell
(74) *Attorney, Agent, or Firm* — Coloplast Corp., Coloplast A/S; Nick Baumann

(57) ABSTRACT

An anal irrigation system and a method for maintenance of an anal irrigation system comprising a tube assembly is disclosed, the method comprising a container and a tube assembly, the method comprising: providing instructions instructing a user to arrange a distal end of the tube assembly in the container for forming a liquid path and to fill liquid into the container; detecting liquid in the container; initiating a disinfection procedure, the disinfection procedure comprises; circulating the liquid in the liquid path for one or more cycles, the one or more cycles comprise one or more liquid circulations; providing instructions instructing the user to discharge liquid from the liquid path.

15 Claims, 3 Drawing Sheets

(52) U.S. Cl.
     CPC ...... *A61L 2202/24* (2013.01); *A61M 2209/10*
              (2013.01); *A61M 2210/1067* (2013.01); *B08B*
              *2209/032* (2013.01)

(56)                    References Cited

U.S. PATENT DOCUMENTS

| 5,871,463 | A | 2/1999 | Baker et al. |
| 2005/0183748 | A1 | 8/2005 | Michels et al. |
| 2008/0208172 | A1* | 8/2008 | Marshall ............. A61M 3/0216 |
| | | | 604/540 |
| 2015/0297769 | A1 | 10/2015 | Dobbyn |
| 2017/0296046 | A1* | 10/2017 | King .................... B08B 9/0321 |
| 2018/0228341 | A1* | 8/2018 | Stojalowski .............. A61L 2/18 |
| 2018/0369474 | A1 | 12/2018 | Falleboe et al. |

FOREIGN PATENT DOCUMENTS

| WO | 03033032 | A2 | 4/2003 |
| WO | 17101954 | A1 | 6/2017 |

* cited by examiner

METHOD FOR DISINFECTING AN ANAL IRRIGATION SYSTEM

The present disclosure relates to anal irrigation systems and related methods, and in particular to a method for maintaining of an anal irrigation system.

BACKGROUND

Control of voluntary bowel functions is frequently limited or absent in patients suffering from certain disabilities, such as spinal injuries, multiple sclerosis or spina bifida. Such lack of control of voluntary bowel functions typically results in faecal incontinence or intractable constipation, as patients have significantly reduced ability to sense the presence of faeces in the colon terminal part and the rectum and to sense the evacuation stimulus. Patients having undergone stomal surgery wherein a catheterizable stoma is constructed may suffer from similar difficulties.

It is known to accomplish bowel emptying by irrigation (i.e. flushing) of the rectum or stoma, by an irrigating fluid, such as tap water or saline, which is provided through an single-use catheter with a tip which is configured and sized for insertion into the rectum or stoma, where it remains in a fixed position by an expandable inflation element, such as a balloon.

Despite the use of single-use catheters, anal irrigation systems must be maintained and cleaned in order to reuse parts thereof.

SUMMARY

There is a need for systems and/or methods increasing the safety for a user of an irrigation system and/or simplifying maintenance of an anal irrigation system.

Accordingly, a method for maintaining of an anal irrigation system comprising a container and a tube assembly is disclosed, the method comprising providing instructions instructing a user to arrange a distal end of the tube assembly in the container for forming a liquid path and to fill liquid into the container; detecting liquid in the container; initiating a disinfection procedure, the disinfection procedure comprises; circulating the liquid in the liquid path for one or more cycles, the one or more cycles comprise one or more liquid circulations; providing instructions instructing the user to discharge liquid from the liquid path.

Further, an anal irrigation system is disclosed, the anal irrigation system comprising a container for containing of liquid; a tube assembly with a proximal end connectable to or connected to the container and a distal end adapted to connect to a catheter; a pump operable to pump liquid from the container through the tube assembly; a controller connected to the pump; wherein the anal irrigation system is configured to perform the method for maintaining an anal irrigation system as mentioned above.

The present disclosure provides a simple, efficient, and easy-to-use anal irrigation system with a high degree of safety for a user, in particular a point-of-care anal irrigation system by guiding the user to and ensuring sufficient disinfection of the anal irrigation system. Further, the present disclosure allows or facilitates multiple uses of different components or parts of the anal irrigation system in turn leading to reduced material use.

Further, the present disclosure provides a gentle maintenance of an anal irrigation system thereby subjecting the anal irrigation system and components thereof to reduced wear in turn leading to a longer lifetime, while complying with demands for disinfection.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
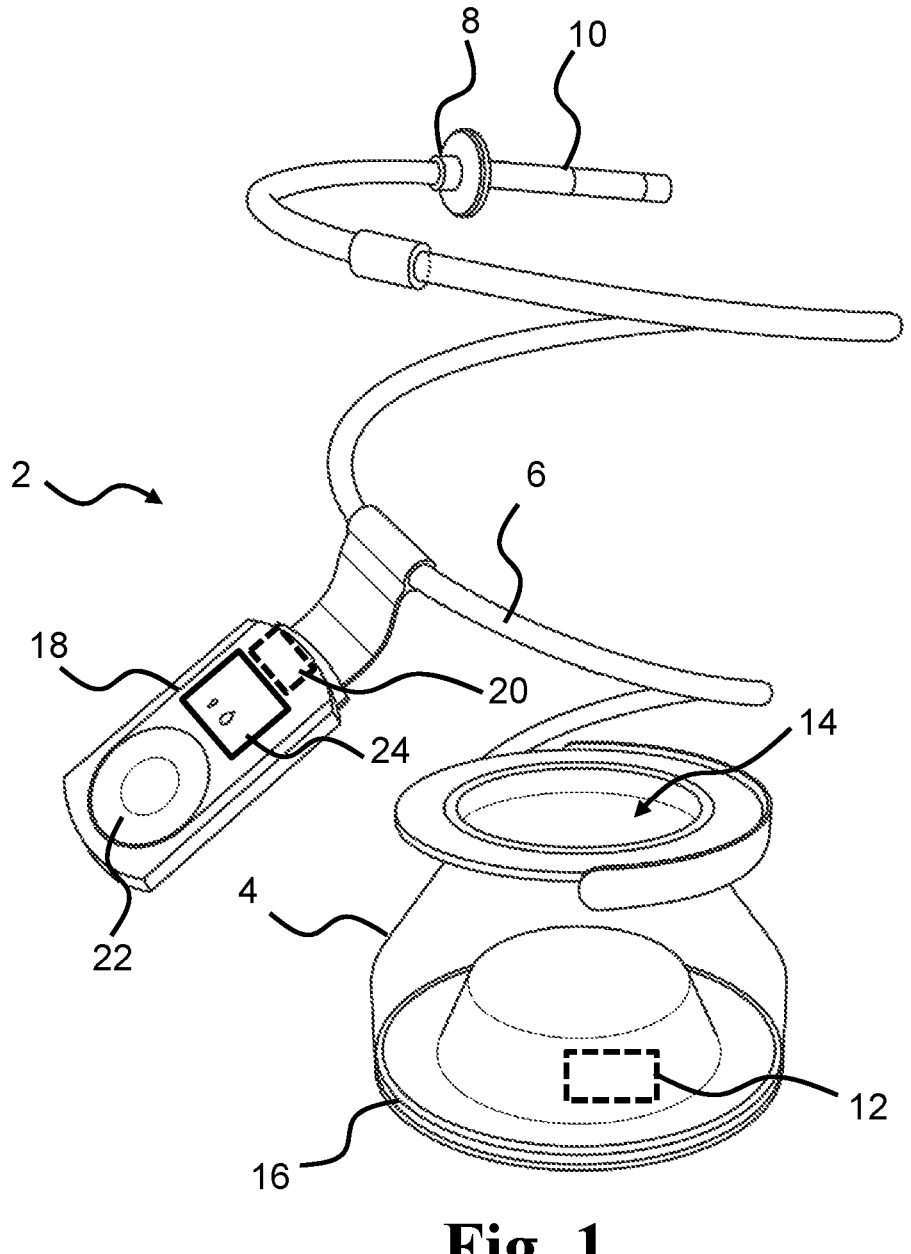
FIG. 1 illustrates an exemplary anal irrigation system.

The present disclosure relates to anal irrigation systems and related methods for maintaining thereof.

A method for maintaining of an anal irrigation system comprising a tube assembly and a container, the method comprising providing instructions instructing a user to arrange a distal end of the tube assembly in the container for forming a liquid path and to fill liquid into the container; detecting liquid in the container; initiating a disinfection procedure, the disinfection procedure comprises; circulating the liquid in the liquid path for one or more cycles, the one or more cycles comprise one or more liquid circulations; providing instructions instructing the user to discharge liquid from the liquid path.

An anal irrigation system is disclosed. The anal irrigation system comprising a container for containing of liquid; a tube assembly with a proximal end connectable to or connected to the container and a distal end adapted to connect to a catheter; a pump operable to pump liquid from the container through the tube assembly; a controller connected to the pump; wherein the anal irrigation system is configured to perform the method for maintaining an anal irrigation system as mentioned above.

Generally, the anal irrigation system is adapted to form a liquid path, when a distal end of the tube assembly is arranged in the container. The anal irrigation system is adapted to circulating the liquid in the liquid path for one or more cycles; and when the distal end of the tube assembly is arranged outside the container, the anal irrigation system is adapted to discharging the liquid from liquid path.

The anal irrigation system may comprise one or more sensors, such as to detect pressure, temperature and/or flow in the anal irrigation system.

The controller may be adapted to activate the pump, control the speed of the pump and control the flow rate in the liquid path of the anal irrigation system. The controller may comprise a memory, such that the controller is adapted to time a duration of one or more periods and to register the number of activities performed by the anal irrigation system.

The tube assembly of the anal irrigation system may comprise at least a first and second lumen, wherein the at least first and second lumen extends in parallel in the longitudinal direction within the tube assembly.

The controller is configured to when a distal end of the tube assembly is arranged in the container for forming a liquid path, perform a disinfection procedure, the disinfection procedure comprising circulating the liquid in the liquid path for one or more cycles; and when the distal end of the tube assembly is arranged outside the container, the controller is configured to discharge liquid from the container.

The liquid may be discharged from the liquid path by pumping the liquid from the container through the tube assembly to the distal end of the tube assembly. After the disinfection procedure a rinsing procedure comprising rinsing the tube assembly may be performed. The methods disclosed may at least partly be performed by an anal irrigation system as disclosed herein.

Generally, the method for maintaining of an anal irrigation system further comprises checking for errors prior to initiating the disinfection procedure, errors being such that the disinfection procedure cannot be performed completely.

The errors may be such as low battery and/or fluid quantity is too low. An error may also be lack of action from user prior to new steps to be performed by the method/anal irrigation system, e.g. user instruction has not been completed by the user e.g. the system detects that the catheter is still connected to the tube assembly, or liquid has not been introduced into the container.

Generally, a set of instruction for use (IFU) may be provided by the method and/or with the anal irrigation system.

In one or more exemplary methods, the disinfection procedure may further comprise: providing instructions instructing the user to add a composition, such as one or more tablets, to the liquid and timing a dissolution period followed by timing a disinfection period and circulating the liquid with the composition in the liquid path for the one or more cycles.

The liquid may be water, such as tap water or distilled water. The liquid may be a disinfection liquid customized to the system. The composition may comprise one or more active agents, such as one or more disinfectants.

In one or more exemplary methods/anal irrigation systems, the disinfection procedure has a duration in the range from 5 minutes to 60 minutes. The disinfection procedure may have a duration in the range from 10 minutes to 30 minutes, such as 20 minutes, to allow sufficient disinfection while maintaining an acceptable wear on the anal irrigation system due to the aggressive liquid used in the disinfection procedure.

The disinfection procedure may comprise one or more cycles, e.g. including at least a first cycle and optionally a second or third cycle. A cycle, such as the first cycle and/or the second cycle, may comprise one or more circulation periods.

The disinfection procedure may have a duration in the range from 5 minutes to 60 minutes for the dissolution period and the disinfection period.

The dissolution period may have a duration in the range from 1 minute to 15 minutes and the disinfection period may have a duration in the range from 1 minute to 30 minutes.

Generally, the dissolution period may have a duration in the range from 1 minute to 15 minutes. The dissolution period may have a length or duration in the range from 2 to 10 minutes, such as from 4 to 8 minutes, e.g. about 6 minutes.

During the dissolution period the pump may be deactivated or operated at a low flow rate, e.g. less than a threshold. The dissolution period may ensure that the composition, such as a tablet is fully dissolved in the liquid to be circulated, e.g. to ensure that tablet residues are not circulated into the tube assembly.

The method may comprise pausing during the dissolution period and not circulating the liquid in the liquid path.

In one or more exemplary methods/anal irrigation systems, a first circulation period may have a duration in the range from 1 minute to 30 minutes. The first circulation period may have a duration in the range from 5 minutes to 20 minutes, such as about 10 minutes or about 15 minutes. A circulation period may be characterized by a constant or slightly varying flow rate of circulated liquid. In one or more exemplary methods/anal irrigation systems, a circulation period, such as the first circulation period, may be characterized by a flow rate of the circulating liquid larger than a threshold, such as larger than 100 ml(milliliter)/minute or larger than 200 ml/minute. The first circulation period may be characterized by a flow rate of the circulating liquid in the range from 500 ml/minute to 1,000 ml/minute.

The first cycle may comprise a pause, optionally followed by one or more circulation periods, e.g. a secondary circulation period and/or a tertiary circulation period. The pause may have a duration larger than 10 seconds, e.g. in the range from 20 seconds to 15 minutes. The pause may have a length or duration in the range from 1 minute to 10 minutes. The first pause may be characterized by no or low degree of circulation of liquid. Thus, the pump may be deactivated or operated at a low flow rate, e.g. less that a threshold, in the first pause.

The method may comprise pausing during the disinfection period and not circulating the liquid in the liquid path.

A pause may allow the liquid with composition to work and disinfect surfaces in the anal irrigation system.

The first cycle of the disinfection procedure may comprise a secondary circulation period. In one or more exemplary methods/anal irrigation systems, the secondary circulation period has a duration in the range from 1 minute to 30 minutes. The secondary circulation period may have a duration in the range from 2 minutes to 20 minutes, such as in the range from 3 minutes to 10 minutes, e.g. about 5 minutes or about 8 minutes. The secondary circulation period may be characterized by a flow rate of the circulating liquid larger than 100 ml/minute, e.g. larger than 200 ml/minute, such as in the range from 500 ml/minute to 1,000 ml/minute.

In the first cycle, the liquid may be circulated for a total circulation time (accumulated time of first circulation period(s)) of in the range from 5 minutes to 30 minutes.

In one or more exemplary methods, the tube assembly comprises at least a first and a second lumen, the at least first and second lumen extends in parallel in the longitudinal direction within the tube assembly, the method comprises the steps of: controlling the liquid flow in the liquid path during circulation and/or discharging of liquid by having flow of liquid in the at least first lumen and subsequently in the second lumen or simultaneously through the at least first lumen and second lumen of the tube assembly.

For example, circulating the liquid in the liquid path may comprise circulating the liquid through the first lumen while not circulating (or at least circulating with a low flow rate) the liquid through the second lumen. For example, circulating the liquid in the liquid path may comprise circulating the liquid through the second lumen while not circulating (or at least circulating with a low flow rate) the liquid through the first lumen. This can be obtained by sequentially blocking or closing the first lumen and/or the second lumen to control and ensure liquid flow (and thus disinfection) of the respective lumen. For example, circulation of liquid in the liquid path may circulate with liquid flow in all parallel lumens in the tube assembly simultaneously.

In one or more exemplary methods, circulating the liquid in the liquid path for one or more cycles comprises circulating the liquid for a second cycle.

In one or more exemplary methods/anal irrigation systems, the rinsing procedure comprises initiating a rinsing procedure, the rinsing procedure comprising: providing instructions instructing the user to add liquid into the container, detecting liquid in the container, timing a rinsing period and circulating the liquid in the liquid path for one or more cycles, the one or more cycles comprise one or more liquid circulations, provide instructions instructing the user to discharge the liquid from the liquid path.

The method may comprise repeating the rinsing procedure for a second cycle or more cycles, such as three or four cycles.

The rinsing procedure may comprise a first rinsing cycle may comprise a first filling of the container with liquid, e.g. with a first volume of liquid, followed by a first discharge of liquid from the container through the tube assembly.

The volume for the rinsing procedure may be at least 300 ml of liquid, e.g. in the range from 500 ml to 2 L of liquid, such as tap water or a rinsing liquid. The discharge of liquid may comprise discharging the liquid through the at least first lumen and/or the second lumen of the tube assembly simultaneously.

Alternatively, the first discharge of liquid may comprise discharging the liquid through the first lumen while not discharging (or at least discharging with a low flow rate) the liquid through the second lumen. For example, the first discharge of liquid may comprise discharging the liquid through the second lumen while not discharging (or at least discharging with a low flow rate) the liquid through the first lumen. This can be obtained by sequentially blocking or closing the first lumen and/or the second lumen to control and ensure effective (first) rinsing of the respective first lumen and second lumen. In one or more exemplary methods/anal irrigation systems, the first rinsing cycle comprises a first circulation of the liquid in the anal irrigation system prior to the first discharge of liquid.

The rinsing procedure may comprise a second rinsing cycle comprises a second filling of the container with liquid, e.g. with a second volume of liquid, followed by a second discharge of liquid from the container through the tube assembly. The second volume may be at least 300 ml of liquid, e.g. in the range from 500 ml to 2 L of liquid, such as tap water or a rinsing liquid. The second discharge of liquid may comprise discharging the liquid through the first lumen and/or the second lumen of the tube assembly, wherein the first lumen and the second lumen are parallel. For example, the second discharge of liquid may comprise discharging the liquid through the first lumen while not discharging (or at least discharging with a low flow rate) the liquid through the second lumen. For example, the second discharge of liquid may comprise discharging the liquid through the second lumen while not discharging (or at least discharging with a low flow rate) the liquid through the first lumen. This can be obtained by sequentially blocking or closing the first lumen and/or the second lumen to control and ensure effective (second) rinsing of the respective first lumen and second lumen. For example, the second discharge of liquid may comprise discharging the liquid trough all parallel lumens simultaneously.

In one or more exemplary methods/anal irrigation systems, the second rinsing cycle comprises a second circulation of the liquid in the anal irrigation system through the tube assembly prior to the second discharge of liquid.

Generally, the pump may—after the discharge of liquid—pump for extra time, when no more liquid is detected to empty the liquid path of the anal irrigation system completely.

In one or more exemplary methods/anal irrigation systems, the method further comprises determining if a dissolution, disinfection or rinsing period complete criterion is satisfied, and in accordance with the dissolution, disinfection or rinsing period complete criterion being satisfied, outputting a complete signal indicative of completion of the period.

The disinfection procedure may comprise determining if a disinfection complete criterion is satisfied, and in accordance with the disinfection complete criterion being satisfied, outputting a disinfection complete signal indicative of completion of the disinfection procedure. Thereby, further operation of the anal irrigation system can be controlled based on, e.g. in dependence of, whether a successful disinfection procedure is detected. Outputting a disinfection complete signal indicative of completion of the disinfection procedure may comprise storing and/or updating an indicator, such as a flag or counter, in the memory of the controller. Outputting a disinfection complete signal indicative of completion of the disinfection procedure may comprise displaying a disinfection complete user interface on the display of the user interface of the anal irrigation system. Outputting a disinfection complete signal indicative of completion of the disinfection procedure may comprise storing a time stamp indicative of time of completion of the disinfection procedure in the memory of the controller.

The rinsing procedure may comprise determining if a rinsing complete criterion is satisfied, and in accordance with the rinsing complete criterion being satisfied, outputting a rinsing complete signal indicative of completion of the rinsing procedure or parts thereof, such as completion of a rinsing cycle. Determining if a rinsing complete criterion is satisfied may comprise determining if a first rinsing complete criterion is satisfied after the first rinsing cycle, and in accordance with the first rinsing complete criterion being satisfied, outputting a first rinsing complete signal indicative of completion of the first rinsing cycle. Outputting a first rinsing complete signal indicative of completion of the rinsing procedure may comprise storing and/or updating an indicator, such as a flag or counter, in the memory of the controller. Outputting a first rinsing complete signal indicative of completion of the first rinsing cycle may comprise displaying a first rinsing complete user interface on the display of the user interface of the anal irrigation system. Outputting a first rinsing complete signal indicative of completion of the rinsing procedure may comprise storing a time stamp indicative of time of completion of the first rinsing cycle in the memory of the controller.

In one or more exemplary methods, the method comprises determining if a maintenance criterion is satisfied, and in accordance with the maintenance criterion being satisfied, requesting maintenance of the anal irrigation system. Requesting maintenance of the anal irrigation system may comprise displaying a maintenance user interface on the display of the user interface of the anal irrigation system. Requesting maintenance of the anal irrigation system may comprise preventing normal operation (irrigation procedure) of the anal irrigation system, e.g. by storing and/or updating a maintenance indicator, such as a flag or counter, in the memory of the controller. The maintenance criterion may be based on time since last maintenance, i.e. time since last completion of the rinsing procedure, and/or a number of irrigation cycles since last maintenance. The maintenance criterion may be satisfied if the time since last maintenance exceeds a time threshold, such as 30 days, or if the number or irrigation cycles since last maintenance exceeds an irrigation cycle threshold, e.g. 30 procedures. The maintenance criterion may be based on one or more error indicators indicative of errors in previous disinfection procedure/rinsing procedure. The maintenance criterion may be satisfied if an error indicator is indicative of error in previous disinfection procedure/rinsing procedure.

The method may comprise determining if a maintenance complete criterion is satisfied, and in accordance with the maintenance complete criterion being satisfied, displaying a maintenance complete user interface on the display of the user interface of the anal irrigation system and/or storing and/or updating (e.g. resetting) a maintenance indicator, such as a flag or counter, in the memory of the controller.

In one or more exemplary methods, the method comprises, after outputting the rinsing complete signal indicative of completion of the rinsing procedure, outputting a maintenance complete signal indicative of completion of the maintenance procedure. Outputting a maintenance complete signal may comprise displaying a maintenance complete user interface on the display of the user interface of the anal irrigation system and/or storing and/or updating (e.g. resetting) a maintenance indicator, such as a flag or counter, in the memory of the controller. Outputting a maintenance complete signal indicative of completion of the maintenance procedure may comprise storing a time stamp indicative of time of completion of the maintenance procedure in the memory of the controller.

In one or more exemplary methods/anal irrigation systems, performing the disinfection procedure comprises determining if a disinfection error criterion is satisfied, and in accordance with the disinfection error criterion being satisfied, outputting a disinfection error signal indicative of error of the disinfection procedure. Thereby, a failsafe disinfection procedure is provided for. Performing the disinfection procedure may comprise detecting a pressure level in the anal irrigation system, such as in the pump and/or in the tube assembly, wherein the disinfection error criterion is based on the pressure level. In one or more exemplary methods/anal irrigation systems, the disinfection error criterion is satisfied if the pressure level, e.g. during the disinfection procedure, is larger than a pressure threshold. A large pressure in the anal irrigation system during the disinfection procedure may indicate kinking of the tube assembly or that a catheter is mounted on the tube assembly (and thereby preventing satisfactory/required disinfection). In one or more exemplary methods/anal irrigation systems, the disinfection error criterion is satisfied if a power consumption of the pump, e.g. during the disinfection procedure is larger than a power threshold. A large power consumption of the pump may be indicative of kinking of the tube assembly or that a catheter is mounted on the tube assembly (and thereby preventing satisfactory/required disinfection). Registration of uneven pressure levels in the system, or uneven pumping may indicate air circulating in the system.

Outputting a disinfection error signal, e.g. indicative of error during the disinfection procedure, may comprise storing and/or updating an error indicator, such as a flag or counter, in the memory of the controller. Outputting a disinfection error signal indicative of error of the disinfection procedure may comprise displaying a disinfection error user interface on the display of the user interface of the anal irrigation system. Performing the disinfection procedure may comprise detecting a power level, such as a battery power level, in the anal irrigation system, wherein the disinfection error criterion is based on the power level. In one or more exemplary methods/anal irrigation systems, the disinfection error criterion is satisfied if the power level, e.g. during the disinfection procedure, is less than a power threshold. Thereby it can be ensured that the anal irrigation system can have sufficient power for performing a desired shut-down procedure, thus avoiding undesired and immediate shut-down of the anal irrigation system due to power outage.

In one or more exemplary methods/anal irrigation systems, performing the rinsing procedure comprises determining if a rinsing error criterion is satisfied, and in accordance with the rinsing error criterion being satisfied, outputting a rinsing error signal indicative of error of the rinsing procedure. Thereby, a failsafe rinsing procedure is provided for. Performing the rinsing procedure may comprise detecting a pressure level in the anal irrigation system, such as in the pump and/or in the tube assembly, wherein the rinsing error criterion is based on the pressure level. In one or more exemplary methods/anal irrigation systems, the rinsing error criterion is satisfied if the pressure level, e.g. during the rinsing procedure, is larger than a pressure threshold. A large pressure in the anal irrigation system during the rinsing procedure may indicate kinking of the tube assembly or that a catheter is mounted on the tube assembly (and thereby preventing satisfactory/required disinfection). In one or more exemplary methods/anal irrigation systems, the rinsing error criterion is satisfied if a power consumption of the pump, e.g. during the rinsing procedure is larger than a power threshold. A large power consumption of the pump may be indicative of kinking of the tube assembly or that a catheter is mounted on the tube assembly (and thereby preventing satisfactory/required rinsing). Outputting a rinsing error signal, e.g. indicative of error during the rinsing procedure, may comprise storing and/or updating an error indicator, such as a flag or counter, in the memory of the controller. Outputting a rinsing error signal indicative of error of the rinsing procedure may comprise displaying a rinsing error user interface on the display of the user interface of the anal irrigation system. Performing the rinsing procedure may comprise detecting a power level, such as a battery power level, in the anal irrigation system, wherein the rinsing error criterion is based on the power level. In one or more exemplary methods/anal irrigation systems, the rinsing error criterion is satisfied if the power level, e.g. during the rinsing procedure, is less than a power threshold. Thereby it can be ensured that the anal irrigation system can have sufficient power for performing a desired shut-down procedure, thus avoiding undesired and immediate shut-down of the anal irrigation system due to power outage.

The method may comprise performing a preparation procedure prior to performing the disinfection procedure. Filling a liquid into the container may form a part of the preparation procedure. Performing the preparation procedure may comprise determining if one or more preparation criteria are satisfied, and in accordance with the one or more preparation criteria being satisfied, proceeding to performing the disinfection procedure. A first preparation criteria may be indicative of correct temperature of the liquid. A second preparation criteria may be indicative of sufficient power to perform the maintenance correct temperature of the liquid. A third preparation criteria may be indicative of sufficient volume of liquid in the container and/or reservoir.

FIG. 1 shows an exemplary anal irrigation system. The anal irrigation system 2 comprises a container 4; a tube assembly 6 with a distal end 8 and a proximal end. The proximal end of the tube assembly 6 is connectable or connected to the container 4 and the distal end 8 of the tube assembly 6 is connectable or releasably coupled to a catheter 10. Typically, the catheter 10 is a single-use catheter that is replaced after each irrigation cycle. The anal irrigation system 2 comprises a pump 12 operable to pump liquid from the container 4 through the tube assembly 6. In other words, a reservoir 14 of the container 4 holds a liquid, and the pump 12 is configured to pump liquid from the reservoir through the proximal end of the tube assembly 6 to the distal end 8 of the tube assembly 6. The pump 12 is arranged in a bottom part 16 of the container 4; however, the pump 12 may be arranged in other parts of the anal irrigation system 2, such as in a user interface housing 18. The anal irrigation system 2 comprises a controller 20 electrically connected to the pump 12 for controlling the operation of the pump. As shown in FIG. 1, the controller 20 is arranged in the user interface housing 18, however the controller 20 may be arranged in other parts of the anal irrigation system 2, such as in the (bottom part 16 of) container 4. The anal irrigation system comprises a user interface 22. The user interface 22 comprises a display 24 and optionally one or more push buttons. The display 24 may be a touch-sensitive display for receiving user input from a user. When the distal end 8 of the tube assembly 6 is arranged in the container 4 (in the reservoir 14), a liquid path is formed by the reservoir 14 of the container 4 through the tube assembly 6 and into the reservoir, thus allowing liquid to be circulated in the anal irrigation system by the pump 12 pumping liquid from the reservoir 14 through the tube assembly 6 such that the liquid is discharged from the distal end 8 of the tube assembly 6 into the reservoir 14.

The tube assembly may comprise at least a first and second lumen, wherein the at least first and second lumen extends in parallel in the longitudinal direction within the tube assembly.

Figure 2:
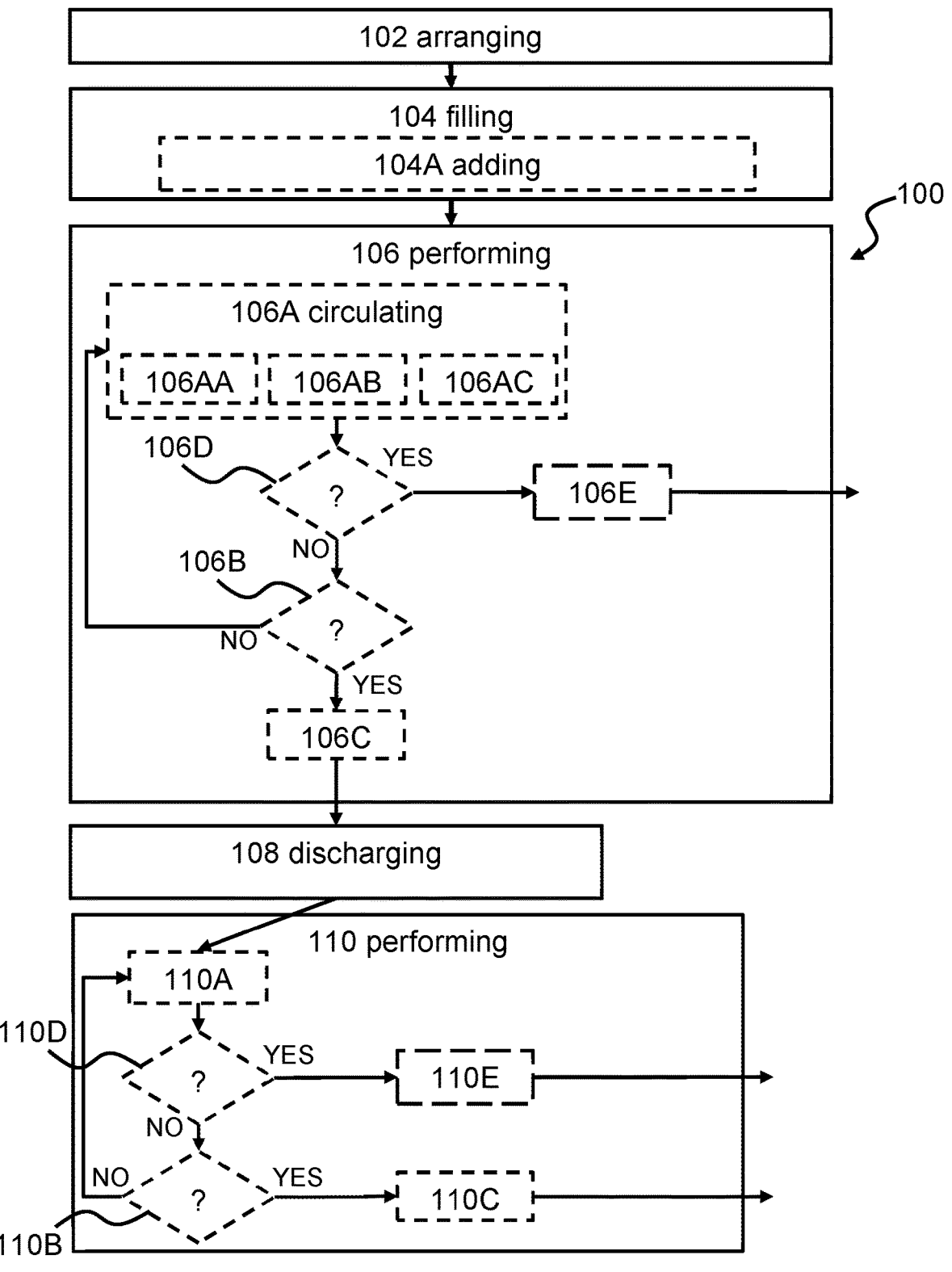
FIG. 2 is a flow chart of an exemplary method for maintaining of an anal irrigation system.

FIG. 2 shows a flow chart of an exemplary method 100 for maintenance of an anal irrigation system, such as anal irrigation system 2. Generally, the method comprises a disinfection procedure followed by a rinsing procedure. The method 100 comprises arranging a distal end of the tube assembly 6 in a container for forming a liquid path 102; filling a liquid into the container 104; performing a disinfection procedure 106 comprising circulating the liquid in the liquid path 106A for one or more cycles including circulating the liquid in the liquid path for a first cycle 106AA; discharging liquid from the container 108; and performing a rinsing procedure 110 comprising rinsing the tube assembly 110A. The disinfection procedure has a duration in the range from 5 minutes to 60 minutes, such as 21 minutes. Filing a liquid into the container 104 optionally comprises adding a composition to the liquid 104A. The first cycle comprises a first dissolution period with a duration of 6 minutes and followed by a first primary circulation period of 15 minutes. Optionally, the first cycle comprises a first pause with no or little circulation allowing the composition with disinfectants to set and work on the surfaces of the anal irrigation system to be disinfected. Circulating the liquid in the liquid path 106A may comprise circulating the liquid through a first lumen and a second lumen of the tube assembly 106AB, wherein the first lumen and the second lumen are parallel. Optionally, circulating the liquid in the liquid path 106A for one or more cycles comprises circulating the liquid for a second cycle 106AC.

In method 100, the rinsing procedure comprises a first rinsing cycle and a second rinsing cycle, the first rinsing cycle comprising a first filling of the container with liquid followed by a first discharge of liquid from the container through the tube assembly, and the second rinsing cycle comprising a second filling of the container with liquid followed by a second discharge of liquid from the container through the tube assembly. By discharging the liquid from the container through the tube assembly, the anal irrigation system is rinsed to remove any residues of active agents in the composition/liquid used in the disinfection procedure.

In method 100, performing the disinfection procedure 106 comprises determining if a disinfection complete criterion is satisfied 106B, and in accordance with the disinfection complete criterion being satisfied, outputting a disinfection complete signal 106C indicative of completion of the disinfection procedure.

In method 100, performing the disinfection procedure 106 optionally comprises determining if a disinfection error criterion is satisfied 106D, and in accordance with the disinfection error criterion being satisfied, outputting a disinfection error signal 106E indicative of error of the disinfection procedure. During the disinfection procedure, a pressure level is detected in the anal irrigation system, and the disinfection error criterion is optionally based on the pressure level, e.g. the disinfection error criterion may be satisfied if the pressure level is larger than a pressure threshold.

Outputting a disinfection error signal 106E may comprise storing and/or updating an error indicator, such as a flag or counter, in the memory of the controller. Outputting a disinfection error signal indicative of error of the disinfection procedure may comprise displaying a disinfection error on the display of the user interface of the anal irrigation system. Outputting a disinfection error signal indicative of error of the disinfection procedure may comprise outputting an audio error signal.

In method 100, performing the rinsing procedure 110 comprises determining if a rinsing complete criterion is satisfied 110B, and in accordance with the rinsing complete criterion being satisfied, outputting a rinsing complete signal indicative of completion of the rinsing procedure 110C.

In method 100, performing the rinsing procedure 110 optionally comprises determining if a rinsing error criterion is satisfied 110D, and in accordance with the rinsing error criterion being satisfied, outputting a rinsing error signal 110E indicative of error of the rinsing procedure.

Outputting a rinsing error signal 110E may comprise storing and/or updating an error indicator, such as a flag or counter, in the memory of the controller. Outputting a rinsing error signal indicative of error of the disinfection procedure may comprise displaying a rinsing error on the display of the user interface of the anal irrigation system. Outputting a rinsing error signal indicative of error of the rinsing procedure may comprise outputting an audio error signal.

Figure 3:
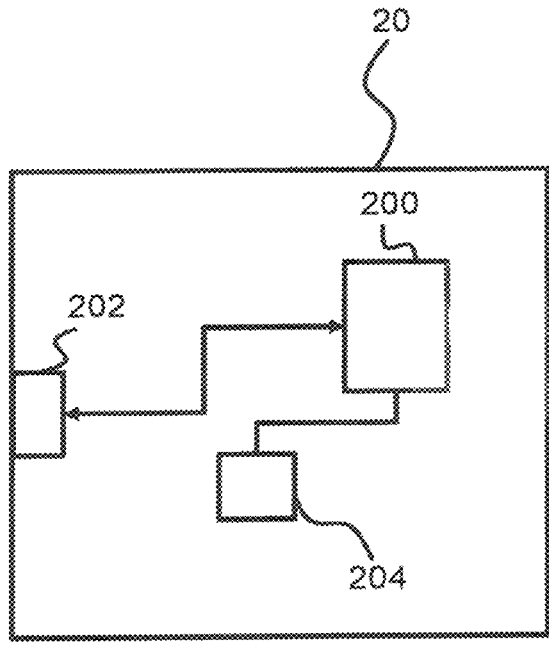
FIG. 3 is a schematic block diagram of a controller of the anal irrigation system.

FIG. 3 is a schematic block diagram of a controller of the anal irrigation system. The controller 20 comprises a processor 200, an interface 202, and a memory 204. The interface 202 is wired or connected to the user interface 22 including the display 24 for receiving user input and outputting feedback to the user regarding the dynamic internal state or operating state of the anal irrigation system 2. Further, the interface is wired or connected to one or more sensors of the anal irrigation system, the one or more sensors optionally including one or more pressure sensors and/or one or more temperature sensors. Further, the interface is optionally wired or connected to one or more valves of the anal irrigation system for controlling the valve (open/closed). The controller 20 is configured to, when the distal end 8 of the tube assembly 6 is arranged in the container 4 (reservoir 14) for forming a liquid path, perform a disinfection procedure, the disinfection procedure comprising circulating the liquid in the liquid path for one or more cycles including a first cycle; and when the distal end of the tube assembly is arranged outside the container, discharging liquid from the container and performing a rinsing procedure comprising rinsing the tube assembly. The disinfection procedure has a duration in the range from 5 minutes to 60 minutes, such as 20 minutes. The first cycle comprises a first dissolution period followed by a first primary circulation period, wherein the first dissolution period has a duration in the range from 1 minute to 15 minutes, such as 6 minutes, and wherein the first primary circulation period has a duration in the range from 1 minute to 30 minutes, such as 15 minutes.

The controller 20 may be configured to, as part of circulating the liquid in the liquid path, circulate the liquid through a first lumen and a second lumen of the tube assembly, wherein the first lumen and the second lumen are parallel. For example, circulating the liquid in the liquid path may comprise circulating the liquid through the first lumen while not circulating (or at least circulating with a low flow rate) the liquid through the second lumen. This may be done by the controller 20 controlling one or more valves of the anal irrigation system in order to block the first lumen and thereby selectively flowing liquid only in the second lumen and not in the first lumen. Further, the controller 20 may be configured to control one or more valves of the anal irrigation system in order to block the second lumen and thereby selectively allow liquid to flow only in the first lumen and not in the second lumen. A corresponding control of the one or more valves may be used in the rinsing procedure for selectively rinsing one lumen while not rinsing the other lumen parallel thereto.

The controller 20 is optionally configured to display one or more user interfaces, e.g. in accordance with different criteria being satisfied as described in more detail above. Further, the controller 20 is optionally configured to store, update, reset one or more indicators and/or one or more timestamps in the memory in accordance with different criteria being satisfied as described in more detail above. The indicator(s) and/or timestamp(s) may serve as operating parameters for the controller, and the controller may be configured to operate the anal irrigation system according to the indicator(s) and/or timestamp(s).

It may be appreciated that FIGS. 1-3 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented.

Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

The invention claimed is:

1. A method for disinfecting an anal irrigation system comprising a tube assembly having a distal end attachable to a body-insertable catheter, the method comprising:

instructing a user using the anal irrigation system on herself or himself to take steps including:

irrigating one of a rectum of the user and a stoma of the user with water drawn from a reservoir and discharged from the body-insertable catheter, removing the body-insertable catheter from a body opening of the user and removing the body-insertable catheter from the distal end of the tube assembly, inserting the distal end of the tube assembly into the reservoir and forming a liquid path out of the reservoir and into a proximal end of the tube assembly connected to the reservoir, through the tube assembly, and out of the distal end of the tube assembly and back into the reservoir such that the liquid path defines a closed loop circulation path within the reservoir;

detecting, with the anal irrigation system, a disinfection liquid in the reservoir;

instructing the user to begin initiating a disinfection procedure for disinfecting portions of the anal irrigation system previously used on herself or himself after removing the body-insertable catheter from the distal end of the tube assembly, the disinfection procedure comprising:

circulating the disinfection liquid through the liquid path for one or more cycles; and instructing the user to discharge the disinfection liquid from the liquid path by withdrawing the distal end of the tube assembly from the reservoir and pumping the disinfection liquid out of the reservoir and out of the tube assembly.

2. The method according to claim 1, further comprising:

adding a disinfecting composition to the disinfection liquid, and timing a dissolution period of the disinfecting composition followed by timing a disinfection period during which the disinfection liquid with the disinfecting composition is circulated along the liquid path.

3. The method according to claim 2, further comprising pausing the dissolution period and not circulating the disinfection liquid in the liquid path.

4. The method according to claim 2, further comprising pausing the disinfection period and not circulating the disinfection liquid in the liquid path.

5. The method according to claim 2, wherein the dissolution period and the disinfection period of the disinfection procedure each has a duration in a range from 5 minutes to 60 minutes.

6. The method according to claim 2, wherein the dissolution period has a duration in a range from 1 minute to 15 minutes.

7. The method according to claim 2, wherein the disinfection period has a duration in a range from 1 minute to 30 minutes.

8. The method according to claim 1, wherein the method further comprises:

initiating a rinsing procedure, wherein the rinsing procedure comprises:

instructing the user to add a second liquid into the reservoir, detecting the second liquid in the reservoir, timing a rinsing period and circulating the second liquid through the liquid path for one or more rinsing cycles, and discharging the second liquid out of the reservoir and the tube assembly and out of the distal end of the tube assembly.

9. The method according to claim 8, comprising repeating the rinsing procedure by repeating the rinsing period.

10. The method according to claim 1, wherein the tube assembly comprises at least a first and a second lumen, the at least first and second lumen extending in parallel in the longitudinal direction within the tube assembly, and wherein the method further comprises:

circulating the disinfection liquid through the first lumen and the second lumen for the one or more cycles.

11. The method according to claim 1, wherein the method further comprises determining if a dissolution period, a disinfection period, and a rinsing period criterion is satisfied, and if satisfied, outputting a complete signal indicative of a completion of the dissolution period, the disinfection period, and the rinsing period.

12. The method according to claim 1, wherein the body-insertable catheter is an anal catheter and the user is a patient experiencing a loss of control of bowel function, the method further comprising:

disinfecting the tube assembly of the system at a point-of-care location of the user.

13. The method according to claim 1, further including determining if a disinfection error criterion is satisfied prior to conclusion of the disinfection procedure.

14. The method according to claim 13, wherein if the disinfection error criterion is not satisfied, the method further includes outputting a disinfection error signal indicative of error of the disinfection procedure.

15. The method of claim 13, wherein the disinfection error criterion is at least one of a pressure level, a fluid level, and a power level.

* * * * *